Figure 1:
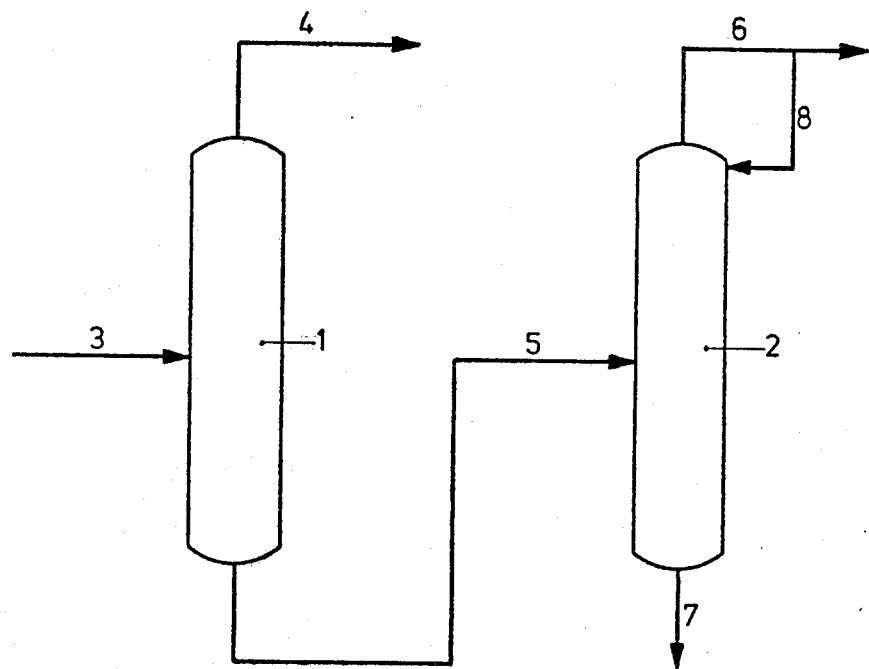

United States Patent [19]

Klenk et al.

[11] 4,313,879

[45] Feb. 2, 1982

[54] PROCESS FOR THE MANUFACTURE OF VERY PURE ε-CAPROLACTONE

[75] Inventors: Herbert Klenk; Rolf Wirthwein, both of Hanau; Gerd Siekmann, Cologne; Wulf Schwerdtel, Leverkusen, all of Fed. Rep. of Germany

[73] Assignees: Degusa AG, Frankfurt am Main; Bayer Aktiengesellschaft, Leverkusen, both of Fed. Rep. of Germany

[21] Appl. No.: 179,622

[22] Filed: Aug. 20, 1980

[30] Foreign Application Priority Data

Aug. 28, 1979 [DE] Fed. Rep. of Germany ....... 2934659

[51] Int. Cl.$^3$ ............................................ C07D 313/04
[52] U.S. Cl. ..................................... 260/343; 203/71; 203/73; 203/78; 203/80
[58] Field of Search .................... 260/343; 203/80, 73, 203/78, 71

[56] References Cited

U.S. PATENT DOCUMENTS 2,875,138  2/1959  Altreuter et al. ...................... 203/80
3,064,008  11/1962  Phillips et al. ....................... 260/343
3,517,033  6/1970  Weiberg .............................. 260/343
3,881,996  5/1975  Schmidt ............................... 203/71

OTHER PUBLICATIONS

Starcher et al., J. A. C. S. 1958, pp. 4079–4081.

*Primary Examiner*—John M. Ford
*Assistant Examiner*—Jane T. Fan
*Attorney, Agent, or Firm*—Sprung, Felfe, Horn, Lynch & Kramer

[57] ABSTRACT

The invention relates to a process for the production of ε-caprolactone having a purity of 99.9% and increased color and storage stability which comprises feeding ε-caprolactone, which has been made by reacting cyclohexanone with a solution of a percarboxylic acid, into a first distillation unit, operating at 0.1 to 500 mbars and drawing off as the top product a mixture consisting of ε-caprolactone and lower-boiling impurities, feeding the bottom product of said first distillation unit into a second distillation unit, operating at 0.1 to 500 mbars and then drawing off the pure ε-caprolactone as the top product. The ε-caprolactone is useful as an intermediate for the production of known useful compounds such as polyesterols which are subsequently converted to polyurethanes.

9 Claims, 1 Drawing Figure

PROCESS FOR THE MANUFACTURE OF VERY PURE ε-CAPROLACTONE

The present invention relates to a continuous process for the industrial production of colour-stable ε-caprolactone from crude ε-caprolactone. This process is only intended for purifying crude ε-caprolactone which has been obtained by reacting cyclohexanone with organic percarboxylic acids.

The organic percarboxylic acids can be present in aqueous or organic solution but are preferably present in organic solution.

The present invention relates in particular to a process for purifying crude ε-caprolactone which has been obtained by reacting organic solutions of perpropionic acid with cyclohexanone.

ε-Caprolactone is an important starting material, for example for the manufacture of polyesterols which are subsequently converted to polyurethanes. However, a possible discoloration of the lactone hinders further processing because the polymerisation products are also discolored.

If ε-caprolactone is prepared from cyclohexanone by previously known processes, by means of a so-called Baeyer-Villiger oxidation, for example with percarboxylic acids (Meth.Chim., 5 (1975), page 697 et seq.), the reaction mixture which is generally obtained essentially contains ε-caprolactone, cyclohexanone and the carboxylic acid from which the peroxycarboxylic acid is derived.

The carboxylic acid from which the peroxycarboxylic acid is derived is preferably a low-molecular carboxylic acid. A reaction mixture of this type is very frequently present in the form of a solution, organic solvents or also water being used as the solvent. ε-Caprolactone is obtained from this solution or this mixture by distillation. The working-up operations can take place continuously or discontinuously.

Thus, for example, according to German patent specification No. 1,258,858, ε-caprolactone is obtained in yields of about 80% after distillation of a reaction mixture containing cyclohexanone, acetic acid, water and ε-caprolactone. The best yield described is 90.5%.

A very similar process is described in DE-AS (German Published Specification) No. 1,693,027. Likewise in this process, the preparation of caprolactone is never described as having a yield higher than 89%, relative to cyclohexanone.

DE-AS (German Published Specification) No. 1,086,686 relates to a process for the preparation of ε-caprolactone in an anhydrous medium. After distillation of a mixture consisting of acetone, cyclohexanone, acetic acid and ε-caprolactone, the yields of ε-caprolactone from this process are also about 80%. The best yield described is 90.3%.

DE-PS (German Patent Specification) No. 1,216,283 and DE-OS (German Published Specification) No. 1,643,146 mention performic acid as the oxidising agent, in which case working-up can be carried out either from an aqueous solution or from an organic solution. The best yield of ε-caprolactone described is 84%.

A review of these known processes shows that, although ε-caprolactone can be prepared with a yield of more than 80%, a yield of 90% can only be achieved rarely and with difficulty. This naturally constitutes a considerable economic disadvantage of these processes.

ε-Caprolactone, manufactured by the known processes, is expected to possess a good storage stability and, in particular, to be stable towards discoloration or towards the formation of acids or towards polymerisation at room temperature or elevated temperature.

However, this is not the case. Thus, for example, it is known from DE-AS (German Published Specification) No. 1,493,317 that even high-grade pure ε-caprolactones are not colour-stable on storage. A freshly distilled ε-caprolactone should be only slightly discolored, but it changes naturally its colour on storage.

Similarly, in the manufacture of polyesterdiols, freshly distilled ε-caprolactone yields slightly discolored products, whereas only strongly coloured polyesterdiols are obtained from the same ε-caprolactone when it has been stored at room temperature for two weeks.

The specialist were therefore very interested in obtaining ε-caprolactone in a form which was stable on storage. For a long time, however, they could only proceed by redistilling even high-grade purified ε-caprolactones before use, for example as described in DE-AS (German Published Specification) No. 1,493,317. No data were given regarding the losses of ε-caprolactone during this distillation, but it is quite obvious that losses, probably even considerable losses, of ε-caprolactone were involved. Because a satisfactory result had obviously not been achieved with the distillation processes used hitherto, it was decided to add, to the ε-caprolactone, certain organic substances possessing a stabilising effect on ε-caprolactone.

Thus, for example, it is known from U.S. Pat. No. 3,227,730 to use triorganophosphites as stabilisers for monomeric ε-caprolactones. However, according to data given in U.S. Pat. No. 3,274,216, the stabilising effect was not adequate, whereupon a mixture of triorganophosphites and alkylphenols was recommended according to the process of the said Patent Specification. The stabilisation operations were carried out predominantly in an inert gas atmosphere.

According to DE-AS (German Published Specification) No. 2,215,909, it is also possible to use triphenylphosphine, for example, as the stabiliser. Stabilisation is again carried out in an inert gas atmosphere.

The stabilisers are preferably used in amounts of 100–1,000 ppm, and this can be a disadvantage when carrying out these processes because higher alkylphenols, or also organophosphorus compounds, in most cases are not readily available commercial products.

When using stabilisers, it can be a disadvantage to mix, with the ε-caprolactone, foreign substances which can occasionally have a drastic effect on the behaviour or the reactivity of the ε-caprolactone. As is known from Makrom. Chem., 56 (1962), 179–194, for example, ε-caprolactone is frequently polymerised in the presence of strongly acid or strongly basic substances. Now, those skilled in the art are familiar with the fact that both phenols and organophosphorus compounds can be very reactive towards acids or bases, if appropriate also in the presence of light, air or heavy metals, and give rise to various decomposition products which, inter alia, are also strongly coloured. According to DOS (German Published Specification) No. 2,160,405, for example, such a mixture of alkylphenols and triorganophosphites, or the addition of triorganophosphites by themselves, also has an adverse effect on the physical properties of the polyurethane product manufactured therefrom. In such cases, an inhibitor can therefore considerably impair the properties of the ε-caprolactone, and the field of application of the ε-caprolactone is restricted.

Another method for the colour stabilisation of ε-caprolactone is given in DE-PS (German Patent Specification) No. 1,956,832. It is known from the said Patent Specification that a colour-stable ε-caprolactone is obtained when the lactone is treated with oxygen and/or one or more oxidising agents and/or one or more acids of low volatility compared with the lactone, and distilled, and the lactone is then treated once again, if appropriate, with an amount of an oxygen-donating compound. However, there is a risk that the caprolactone can very readily polymerise under precisely these conditions and that distillation residues are thereby obtained as losses.

In summarising the processes known hitherto, it must therefore be said that the industrial preparation of ε-caprolactone by the above processes is restricted by two limiting factors. These are firstly the insufficient purity of the product, in particular the colour instability, and secondly the inadequate efficiency as a result of insufficient yields. If measures are taken to improve the colour stability, such as distillation or chemical treatments—as described above—if appropriate with further distillation operations or the addition of stabilisers, these measures are not necessarily successful and they also represent a further reduction in the efficiency of the process in question.

The subject of the Application is a process for increasing the storage stability and colour stability of ε-caprolactone, which process can be carried out without any special technical effort.

It has now been found that very pure ε-caprolactone possessing a high storage stability and colour stability can be obtained from crude ε-caprolactone, which has been obtained by reacting cyclohexanone with a solution of a percarboxylic acid and by subsequently subjecting the reaction mixture to fractional distillation, by feeding crude ε-caprolactone into a first distillation unit, which is operated at a pressure of 0.1 to 500 mbars and at the top of which unit the temperature is set in the range from 10° C. (when the pressure is 0.1 mbar) to 190° C. (when the pressure is 500 mbar), and drawing off, as the top product, a mixture consisting of ε-caprolactone and lower-boiling impurities, and then feeding the bottom product of this distillation unit into a second distillation unit, which is operated at a pressure of 0.1 to 500 mbars and at the top of which unit the temperature is set in the range from 15° C. (when the pressure is 0.1 mbar) to 210° C. (when the pressure is 500 mbar), and drawing off the pure ε-caprolactone as the top product.

Said first distillation unit is preferably operated at a pressure of 5 to 120 mbars and the temperature at its top is preferably set in the range from 70° C. (when the temperature is 5 mbar) to 150° C. (when the pressure is 120 mbar).

Said second distillation unit is preferably operated at a pressure of 5 to 120 mbars and the temperature at its top is preferably set in the range from 85° C. (when the pressure is 5 mbar) to 165° C. (when the pressure is 120 mbar).

"Crude ε-caprolactone" as used herein is understood as meaning lactones which are manufactured by reacting cyclohexanone with percarboxylic acids in aqueous or organic solutions.

However, ε-caprolactones which are obtained with the aid of percarboxylic acids in organic solvents are preferred.

Examples of suitable percarboxylic acids are peralkanoic acids having 1 to 6 carbon atoms such as peracetic acid, perpropionic acid and perbutyric acids.

An ε-caprolactone which has been obtained with the aid of perpropionic acid is preferred.

Although aqueous solutions of the abovementioned percarboxylic acids can be used for reaction with cyclohexanone, organic solutions of these percarboxylic acids are particularly advantageous because they give higher yields of ε-caprolactone. It has been shown that aliphatic, cycloaliphatic and aromatic hydrocarbons, and also their halogen derivatives, are particularly suitable as organic solvents.

The present process is preferably carried out using a solution of perpropionic acid in one of the above-mentioned solvents, in particular in benzene or dichloropropane.

Customary columns with plates or packing are employed as the distillation unit.

As stated, two distillation units are used in the process according to the invention, and the process is in fact designed so that, for example, the crude ε-caprolactone is introduced into the middle or the upper half of the first fractionation column.

Fractionation columns having a number of theoretical plates of at least 6, for example, are suitable for this distillation column of customary design. In general, columns having up to 200 theoretical plates can be used, but distillation columns having 9 to 80 theoretical plates are preferred and those having 12 to 50 theoretical plates are very particularly preferred.

The columns can be heated using the customary evaporator systems; falling film evaporators are particularly suitable. Of the column pressures given above, pressures between 5 and 120 mbars are particularly preferred.

The reflux ratio can vary within unusually wide limits but depends on the other distillation conditions. Normally, the reflux ratios are set at 0.5 to 200, but reflux ratios of 1 to 25 are preferred.

Although the column can be operated in such a way that a large part of the intake can be drawn off as distillate, it is preferred to draw off only small amounts. Normally, at most 10% by weight of the intake, preferably less than 1.5% by weight, is withdrawn as the distillate. The amounts of ε-caprolactone lost, because this withdrawn distillate is frequently no longer worked up in order to obtain ε-caprolactone, are therefore only small in this case.

Customary procedures can be followed for obtaining the distillate and producing the reflux. That is to say that, for example, the distillate can be totally condensed and part of it can be transferred to the column as reflux. However, it is more advantageous to use a partial condensation system such as, for example, a dephlegmator system.

The following compounds are detected in this withdrawn distillate, for example by gas chromatographic/mass spectrometric examination: ε-caprolactone, cyclohexanone and, if appropriate, propionic acid, and also hydroxycyclohexanone, cyclohexenone and cyclohexanedione. Astoundingly, high-boiling substances such as hydroxycyclohexanone dimer, and also a cyclic product of the following structure:

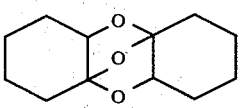

were also found in the withdrawn distillate, that is to say in the low-boiling components.

A possible embodiment of the process involves feeding this withdrawn distillate back into the process for the manufacture of ε-caprolactone. Thereby, the ε-caprolactone drawn off is not lost, and exactly the same applies to the cyclohexanone drawn off. The other compounds are converted to readily separable compounds, mostly by means of spontaneous reactions during the formation of the ε-caprolactone.

That part of the stream, introduced into the first fractionation column, which is not drawn off as distillate is now continuously drawn off from the bottom of this column and, as stated, fed into the middle or the lower half of a second fractionation column. A distillation column of customary design is also suitable in this case, but this column preferably possesses fewer theoretical plates than the first column. In general, 3 to 30 theoretical plates are present. Preferably, there are 1 to 8 theoretical plates in the stripping section and 2 to 22 theoretical plates in the rectifying section.

There are no restrictions as regards the condensation and the reflux production. Thus, for example, a partial condensation system can be used or the rising vapours are totally condensed and part of this condensate is transferred to the column as reflux.

This second column can also be heated using the customary evaporation systems; falling film evaporators or thin film evaporators are particularly suitable.

Although the choice of the pressure in this column is also substantially unrestricted, it is advantageous to choose the same pressure as in the first column, or a similar pressure.

The reflux ratio can vary within wide limits and depends on the other distillation conditions. Normally, however, lower reflux ratios than in the first column are used. In general, a reflux ratio of 0.1 to 5:1 is sufficient. A reflux ratio lying in the range of 0.2 to 3:1 is preferably chosen.

The very pure ε-caprolactone is obtained as the top product of this second column. According to gas chromatographic analysis, its purity is generally higher than 99.99%.

Compounds having higher boiling points than ε-caprolactone can be detected in the bottom of this second column, but most of these are present in amounts of less than 0.1% by weight, relative to the amount of ε-caprolactone fed into the first column. These higher-boiling compounds are continuously drawn off from the bottom of the second column, but they are usually drawn off in the form of a solution in ε-caprolactone. These higher-boiling compounds are preferably present in this solution at concentrations of 0.3 to 30% by weight and very particularly preferably of between 0.6 and 15% by weight.

The solutions drawn off from the second column can be discarded, but they are preferably fed back into the process for the manufacture of crude ε-caprolactone. In this manner, the ε-caprolactone present in the solution can be recovered.

It is very advantageous to carry out the process according to the invention in combination with the process of German Patent Application P 29 20 436.2 corresponding to U.S. Pat. Application Ser. No. 150,260 filed May 15, 1980 which relates to a particularly advantageous preparation of ε-caprolactone.

The process of German Patent Application P 29 20 436.2 consists in (a) reacting a solution of perpropionic acid in an organic solvent, with cyclohexanone, in a molar ratio cyclohexanone: perpropionic acid of 1.1 to 5:1, at temperatures of 10° to 80° C., (b) feeding the resulting reaction mixture, essentially consisting of ε-caprolactone, cyclohexanone, propionic acid and organic solvent, into a first distillation unit, where the organic solvent for the perpropionic acid is recovered as the distillate, (c) transferring the bottom product of the first distillation unit into a second distillation unit, where propionic acid is obtained as the top product, together with cyclohexanone which did not react in step (a), and drawing off ε-caprolactone, and also high-boiling components if appropriate, separately from one another, below the intake into this second distillation unit, and (d) transferring the distillate, consisting of propionic acid and cyclohexanone, from the second distillation unit to a third distillation unit, where a mixture consisting of propionic acid and cyclohexanone is obtained and propionic acid is recovered as the distillate, after which (e) the mixture obtained in step (d) and consisting of cyclohexanone and propionic acid is fed back into reaction step (a).

This circulation of a mixture consisting of propionic acid and cyclohexanone constitutes an essential characteristic of the process of German Patent Application P No. 29 20 436.2.

By combining the process according to the invention with the process of German Patent Application P No. 29 20 436.2, the partial stream drawn off from the bottom of the second column unit, by the process according to the invention, can now be fed back directly into that column of the process of German Patent Application P No. 29 20 436.2 in which the separation of cyclohexanone/propionic acid from ε-caprolactone and the high-boiling components is carried out.

The position for the introduction of this stream into the abovementioned column is arbitrary, but it is advantageously chosen with regard to the concentration. Thus, the introduction of the stream preferably takes place near the bottom of the abovementioned column.

The technical advance of the process according to the invention lies firstly in the fact that, by expanding the distillation plant, which is still necessary for the manufacture of ε-caprolactone, by a small number of units, a truly colour-stable ε-caprolactone can be obtained.

Secondly, there is the fact that the yields are hardly reduced as a result of the multiple distillation operations, because the losses are generally only between about 1 and 2% by weight.

It could not be anticipated that this simple expansion, not carried out hitherto, and the resulting possibility of dividing the distillation of the crude products into several single distillation operations, could enable the by-products, which reduce the storage stability of ε-caprolactone to such a great extent, to be virtually removed from the crude product by means of these single distillation operations, and that a truly colour-stable ε-caprolactone would be obtained in this way.

The invention is also illustrated with the aid of the following examples:

FIG. 1 shows both the process according to the invention in general and also the specific ways in which Examples 1 and 2 are carried out.

EXAMPLE 1: industrial

The apparatus used consists, in continuous operation, of two distillation units 1 and 2, which represent the two-column high-purification system.

In a continuous experiment, 20.48 kg/hour of crude ε-caprolactone are fed into the distillation unit 1 via the line 3.

The distillation unit 1 consists of an 8 m high packed column containing metal pall rings as the packing. The diameter of the column is 15 cm. The stream fed via 3 is introduced 2 m below the top of the column. This column is heated with a falling film evaporator (not shown). A dephlegmator (not shown) is used as the distillation head and, by means of cooling, is regulated so that the rising top vapours are divided so as to give a reflux ratio of 4:1. In this process, the heating is regulated so as to give, via 4, a distillate of 0.25 kg per hour.

During this process, the amount not drawn off as distillate is withdrawn continuously, via 5, from the bottom of this distillation unit 1 and fed into the middle of the distillation unit 2. The distillation unit 2 consists of a 3 m high packed column having a diameter of 20 cm and containing metal pall rings as the packing. This column is heated with a thin film evaporator (not shown). The rising top vapours are totally condensed in a condenser and 12.8 kg/hour of reflux are transferred to the column via the line 8. 18.33 kg/hour of pure ε-caprolactone are also withdrawn from the condensate via 6. 1.9 kg per hour are drawn off from the bottom of the column via the thin film evaporator (not shown) and via 7, and are fed back into the process for the manufacture of caprolactone, where this stream can be separated into high-boiling components and crude ε-caprolactone. Accurate analysis of this stream shows that it consists of 98.95% by weight of ε-caprolactone monomer and 1.05% by weight of higher-boiling compounds.

As can be seen, only 1.3% by weight of the amount of crude lactone fed in is therefore lost as a result of the distillation operations.

The ε-caprolactone which was withdrawn via 6 is 99.99% pure according to gas chromatographic analysis
(2 m 20% SE 52, He as carrier gas, oven temperature 225°, TCD)
(2 m SE 52 = column material—silicone rubber)
(TCD = thermal conductivity detector)

This ε-caprolactone is used to carry out the experiments described in Examples 3 and 4.

EXAMPLE 2

The procedure of Example 1 is followed, except that the distillation unit 1 is modified so that the rising top vapours are totally condensed and flow into a distillate vessel (not shown). 1 kg per hour of liquid phase is transferred from this distillate vessel onto the top of the distillation unit 1 as reflux, and 0.25 kg/hour is drawn off as distillate.

The remaining flow rates and ratios are the same as in Example 1.

Gas chromatographic analysis shows that the ε-caprolactone withdrawn via 6 contains 0.02% of a by-product. This by-product was also found in the distillate withdrawn via 4, whereas it is not present in the crude ε-caprolactone fed in via 3.

By multiple extraction with water, an oily phase is obtained from relatively large amounts of the distillate withdrawn via 4, and the said phase is distilled. At 0.1 mbar and at a boiling point of 130° C., a distillate passes over which, on standing in the cold, yields a few white crystals as a precipitate. These crystals are recrystallised from acetone and have a melting point of 123° C. A mass spectrum gives a molecular weight of 210.

Elementary analysis

| $C_{12}H_{18}O_3$ | C calculated: | 68.54% | found: | 68.62 |
|---|---|---|---|---|
| | H calculated: | 8.63% | found: | 8.69 |

No C=O vibration can be detected in the IR spectrum.
The $^{13}$C-NMR spectrum gives the following signals:
Values in ppm: 22.41 t; 22.89 t; 28.56 t; 32.58 t; 80.86 d; 107.85 s;
t = triplet
d = doublet
s = singlet
This enables the following structure to be deduced:

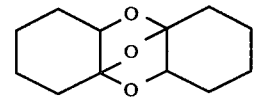

EXAMPLE 3

A crude ε-caprolactone and an ε-caprolactone which was obtained via 6 in accordance with Example 1 possessed, immediately after they had been obtained, a colour index of 10 based on ASTM Standard Specification D No. 1209-54.

Samples of equal weight of each of these compounds were transferred in air into identical flasks and the flasks were sealed. The amount of air was the same in both cases. After standing for 4 weeks at room temperature, the colour index of the samples was examined again. The sample of the ε-caprolactone which had been withdrawn from line 6 still possessed a colour index of 10; in contrast, the sample of crude ε-caprolactone possessed a colour index of about 500.

EXAMPLE 4

Polyesters containing 2 hydroxyl groups (polyesterdiols) were prepared from ε-caprolactone by reaction with a diol, such as ethylene glycol, in the presence of an esterification catalyst, at elevated temperature. The colour values of the products obtained were as follows:

| ε-Caprolactone used | (Colour index) Colour of the polyester-diol |
|---|---|
| 1. ε-Caprolactone withdrawn via 6, freshly obtained | 10 |
| 2. Crude ε-caprolactone, freshly obtained | 10-20 |
| 3. ε-Caprolactone withdrawn via 6, after storage for 4 weeks | 10 |
| 4. Crude ε-caprolactone, after storage for | about 200 |

|ε-Caprolactone used | (Colour index) Colour of the polyester-diol |
|---|---|
| 4 weeks | |

What is claimed is:

1. Process for the production of ε-caprolactone having a purity of 99.9% which comprises feeding ε-caprolactone, which has been made by reacting cyclohexanone with a solution of a percarboxylic acid, into a first distillation unit, which is operated at a pressure of 0.1 to 500 mbars and at the top of which unit the temperature is set in the range from 10° C. (when the pressure is 0.1 mbar) to 190° C. (when the pressure is 500 mbar), drawing off as the top product a mixture consisting of ε-caprolactone and lower-boiling impurities, feeding the bottom product of said first distillation unit into a second distillation unit, which is operated at a pressure of 0.1 to 500 mbars and at the top of which unit the temperature is set in the range from 15° C. (when the pressure is 0.1 mbar) to 210° C. (when the pressure is 500 mbar), then drawing off the pure ε-caprolactone as the top product, the double distillation being carried out so that the reflux ratio in said first distillation unit being set at 0.5 to 200 and the reflex ratio is said second distillation unit being lower than that set for the first distillation unit and set at 0.1 to 5:1.

2. Process according to claim 1 wherein the first distillation unit is operated at a pressure of 5 to 120 mbars and the temperature at its top is set in the range from 70° C. (when the pressure is 5 mbar) to 150° C. (when the pressure is 120 mbar) and the second distillation unit is operated at a pressure of 5 to 120 mbars and the temperature at its top is set in the range from 85° C. (when the pressure is 5 mbar) to 165° C. (when the pressure is 120 mbar).

3. Process according to claims 1 or 2 wherein the percarboxylic acid is peralkanoic acid having 1 to 6 carbon atoms.

4. Process according to claim 3 wherein the peralkanoic acid is perpropionic acid.

5. Process according to claims 1, 2 or 3 characterised in that at most 10% by weight of the intake in the first distillation unit is drawn off as the top product.

6. Process according to claim 1, characterised in that 50 to 97% by weight of the vapours from the first distillation unit is condensed and transferred to the first distillation unit as reflux, and the uncondensed part is liquefied in a separate condenser and withdrawn as distillate.

7. Process according to claims 1, 2 or 3, characterised in that the distillate of the first distillation unit is fed back into the process for the manufacture of ε-caprolactone.

8. Process according to claims 1, 2, 3 or 4, characterised in that the bottom product of the second distillation unit is fed back into the process for the manufacture of ε-caprolactone.

9. Process according to claim 1, characterised in that it comprises (a) reacting a solution of perpropionic acid in an organic solvent, with cyclohexanone, in a molar ratio cyclohexanone: perpropionic acid of 1.1 to 5:1, at temperatures of 10° to 80° C., (b) feeding the resulting reaction mixture, essentially consisting of ε-caprolactone, cyclohexanone, propionic acid and organic solvent, into a first distillation unit, where the organic solvent for the perpropionic acid is recovered as the distillate, (c) transferring the bottom product of the first distillation unit into a second distillation unit, propionic acid is obtained as the top product, together with cyclohexanone which did not react in step (a), and drawing off ε-caprolactone, and also high-boiling components if appropriate, separately from one another, below the intake into this second distillation unit, and (d) transferring the distillate, consisting of propionic acid and cyclohexanone, from the second distillation unit to a third distillation unit, where a mixture consisting of propionic acid and cyclohexanone is obtained and propionic acid is recovered as the distillate, after which (e) the mixture obtained in step (d) and consisting of cyclohexanone and propionic acid is fed back into reaction step (a).

* * * * *